United States Patent
Rubinstein

(10) Patent No.: US 6,547,745 B1
(45) Date of Patent: Apr. 15, 2003

(54) FEVER ALARM SYSTEM

(75) Inventor: Eliahu Rubinstein, 8 Hagdud A'ivri St., Hertzeliya (IL)

(73) Assignee: Eliahu Rubinstein, Hertzeliya (IL)

( * ) Notice: Subject to any disclaimer, the term of this patent is extended or adjusted under 35 U.S.C. 154(b) by 0 days.

(21) Appl. No.: 09/602,232

(22) Filed: Jun. 23, 2000

(30) Foreign Application Priority Data

Jun. 23, 1999 (IL) .................................................. 130625

(51) Int. Cl.[7] .................................................. A61B 5/00
(52) U.S. Cl. ...................................... 600/549; 374/100
(58) Field of Search ............................... 600/549, 474; 128/903; 374/100, 109

(56) References Cited

U.S. PATENT DOCUMENTS

| | | | | |
|---|---|---|---|---|
| 4,306,569 A | * | 12/1981 | Weil et al. | 600/549 |
| 5,050,612 A | * | 9/1991 | Matsumura | 600/483 |
| 5,333,784 A | | 8/1994 | Pompei | 236/91 C |
| 5,441,476 A | * | 8/1995 | Kitado et al. | 600/26 |
| 5,469,855 A | | 11/1995 | Pompei et al. | 600/474 |
| 5,653,239 A | | 8/1997 | Pompei et al. | 600/474 |
| 5,844,862 A | * | 12/1998 | Cocatre-Zilgien | 368/10 |
| 5,938,619 A | * | 8/1999 | Dogre Cuevas | 600/549 |
| 5,967,992 A | | 10/1999 | Canfield | |
| 6,056,435 A | * | 5/2000 | Pompei | 374/133 |
| 6,059,452 A | | 5/2000 | Smith et al. | |
| 6,198,394 B1 | * | 3/2001 | Jacobsen et al. | 340/573.1 |
| 6,286,992 B1 | | 9/2001 | Kyrtsos | |
| 6,292,685 B1 | * | 9/2001 | Pompei | 600/474 |
| 6,402,371 B2 | | 6/2002 | Pompei et al. | |

FOREIGN PATENT DOCUMENTS

| | | |
|---|---|---|
| FR | 2 233 971 | 1/1975 |
| JP | 56162022 | 12/1981 |
| JP | 09201338 | 5/1997 |

* cited by examiner

Primary Examiner—Max F. Hindenburg
Assistant Examiner—Charles Marmor, II
(74) Attorney, Agent, or Firm—Knobbe, Martens, Olson & Bear, LLP

(57) ABSTRACT

A body temperature measurement device includes a unit (2) that continually measures body temperature and transmits the measurement through an RF transmitter (14) to a display unit (30). The display unit (30) includes an RF receiver (37), a processor (33), and a display (35) that shows the temperature. The display unit (30) includes an adjustable threshold alarm circuit that turns on an alarm whenever the temperature rises above a defined threshold.

18 Claims, 4 Drawing Sheets

FEVER ALARM SYSTEM

BACKGROUND OF THE INVENTION

1. Field of the Invention

The present invention is related to a clinical thermometer, and more particularly to a skin thermometer, which performs calculation of oral or rectal temperature. The thermometer is connected to an RF transmitter/receiver system to display the temperature in a remote place and to raise an alarm when the temperature is above a predetermined threshold.

2. Description of the Related Art

Numerous devices for body temperature measurement are known. Some devices measure temperature continuously. U.S. Pat. Nos. 4,509,533, 4,333,477, 4,232,684, 4,030,483 describe skin fever thermometers, but the disclosed thermometers use liquid crystal which changes color according to temperature range. The prior art does not suggest a method for accurate reading and calculation of body (oral and rectal) temperature. The prior art also does not provide a solution for remote reading and remote alarm system when the fever rises above a certain threshold.

SUMMARY OF THE INVENTION

It is the first objective of this invention to provide a solution for accurate, continuous measurement of skin temperature and to accurately calculate body temperature. The temperature measurement device preferably comprises two thermistors. The first thermistor is attached to the skin and is thermally isolated from the surroundings. The other thermistor is thermally isolated from the skin and measures the room ambient temperature. A look-up correlation table in the processor correlates the temperature readings to oral or rectal temperature while taking into consideration the room temperature.

Another objective of this invention is to provide a remote reading of the temperature through a wireless communication link and to sound or activate an alarm whenever the temperature rises above a predetermined threshold.

DETAILED DESCRIPTION OF THE PREFERRED EMBODIMENT

Figure 1:
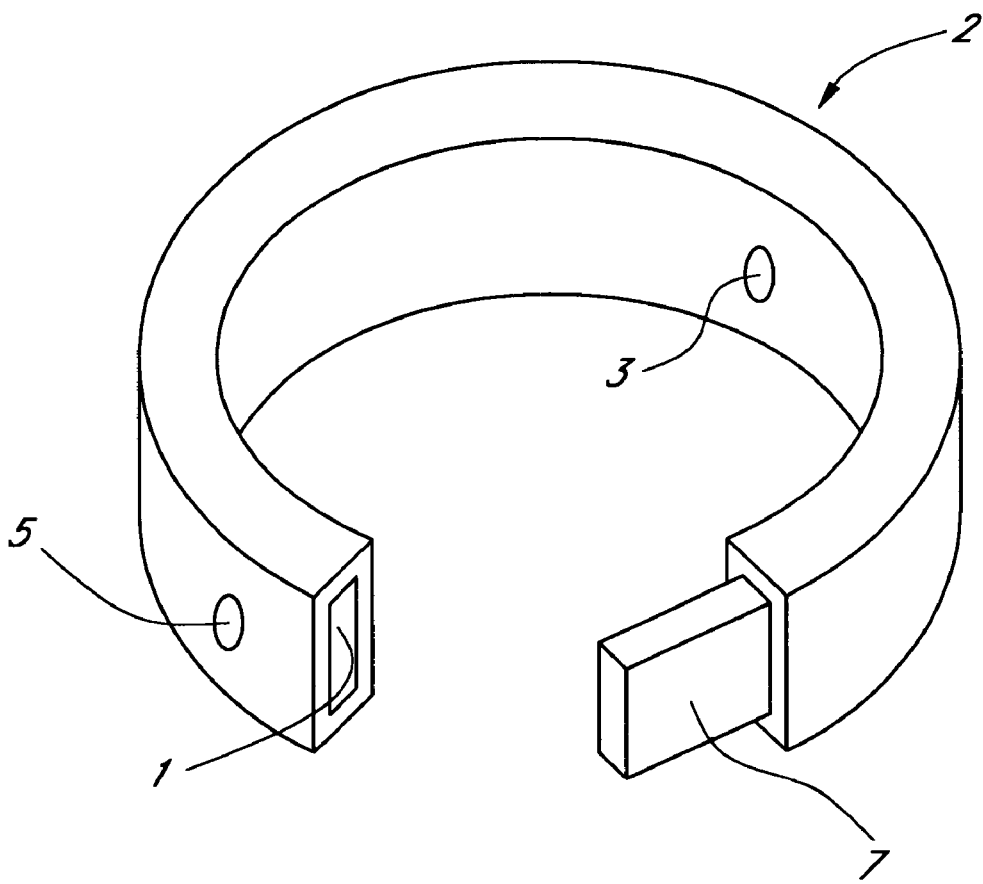
FIG. 1 is a drawing of the wrist temperature measurement device of the preferred embodiment.

FIG. 1 illustrates the general construction of the part of the skin temperature measurement device attached to the body. According to the preferred embodiment, this unit 2 has the shape of the wrist and is made of a soft material with a very low thermal conductivity, such as foamed polyurethane. The unit incorporates a flexible electronic board 1 with a connector 7 that turns the unit on when it closes. Two thermistors 3, 5 are assembled on the electronic board. The thermistor 3 faces the skin side and is attached to the skin while being thermally isolated from the ambient room temperature by the polyurethane. The thermistor 5 faces away from the wrist and is thermally isolated from the skin in order to measure the immediate ambient temperature surrounding the skin. The flexible printed board 1 also has an RF antenna printed on the board itself. A soft disposable pad can be attached to the inner side of the unit in order to keep the unit hygienically clean.

Figure 2:
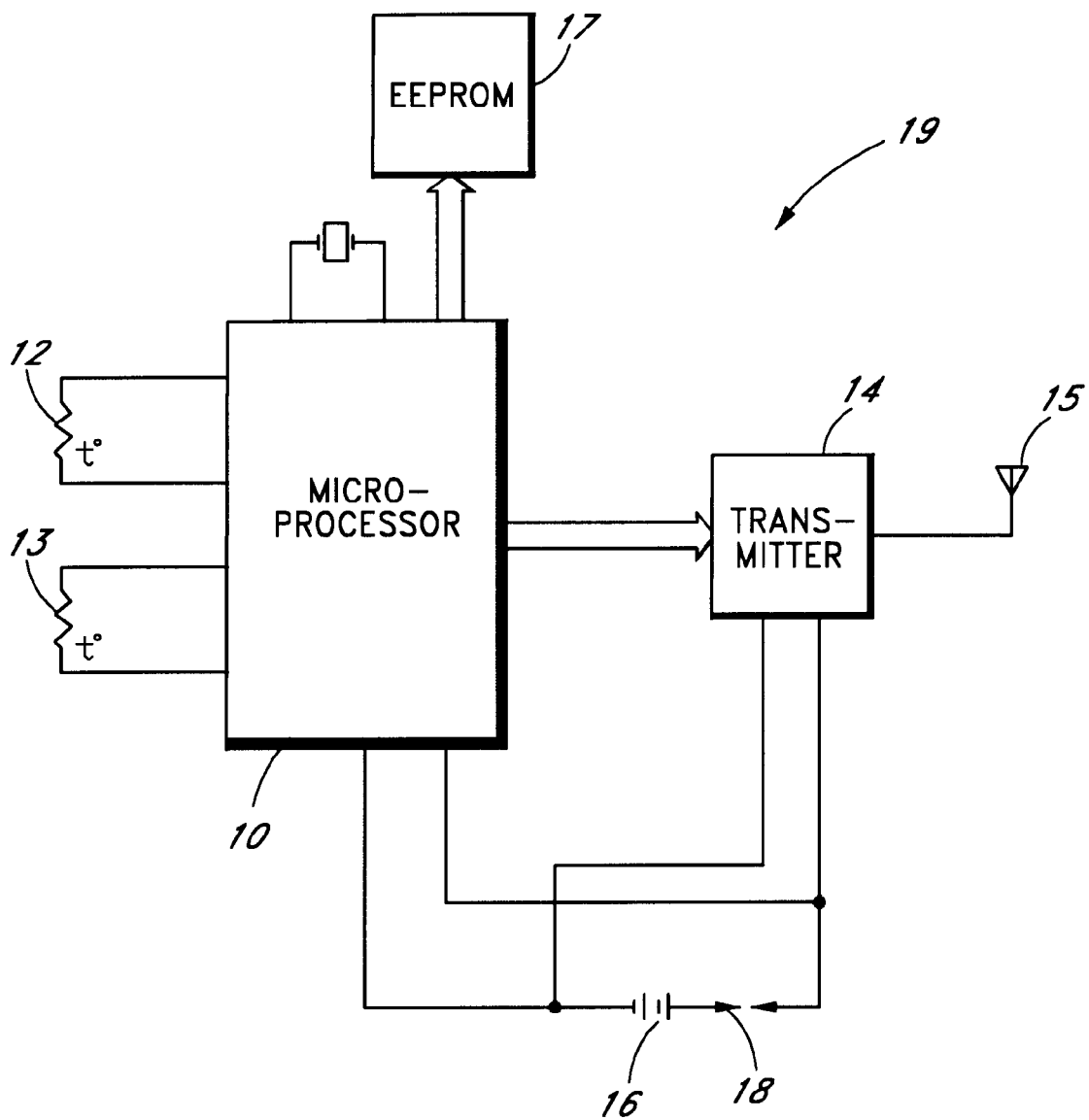
FIG. 2 is a schematic electronic drawing of the measurement unit of the preferred embodiment.
Figure 5:
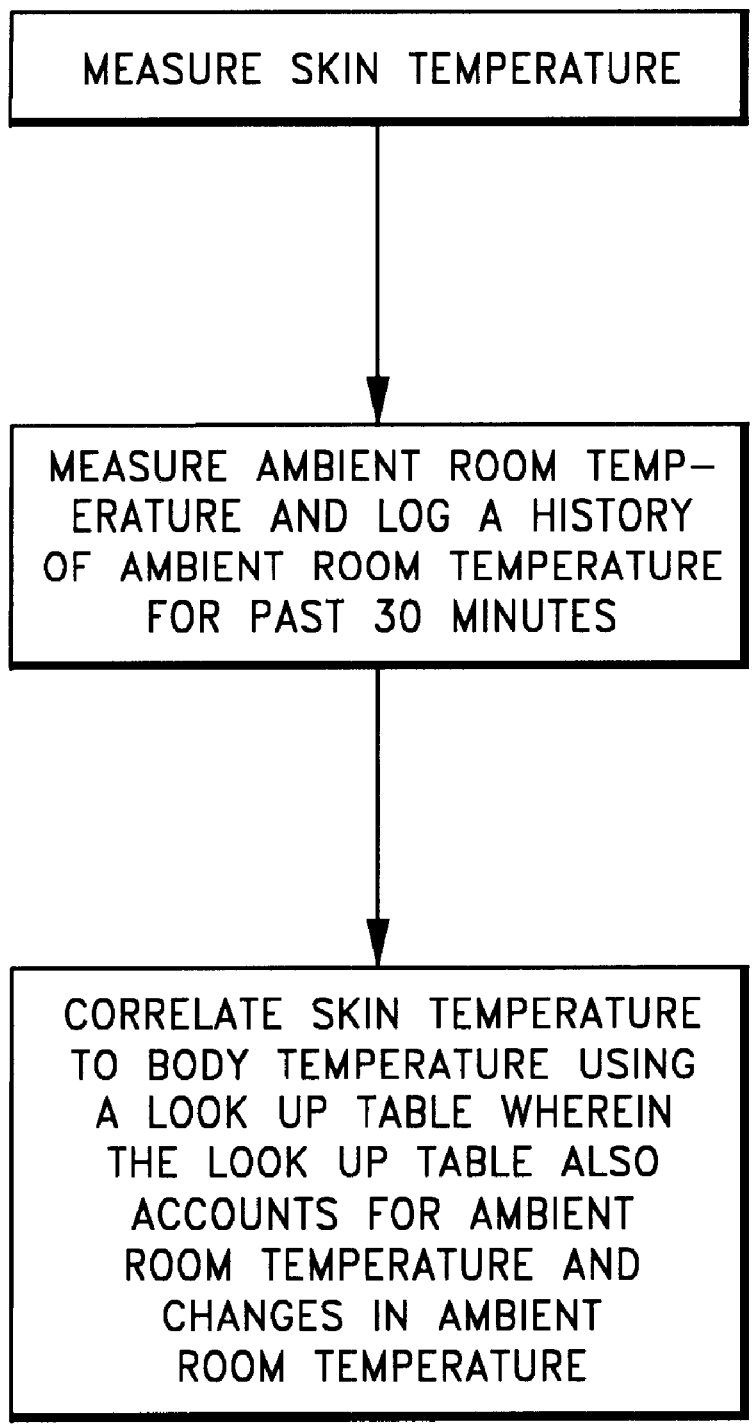
FIG. 5 illustrates a method for calculating body temperature.

FIG. 2 shows a schematic circuit diagram of the electronic unit 19 of the device attached to the skin. A microprocessor or processing unit 10 preferably includes two resistance-to-frequency converters, such as series 6200 made by Epson, Japan. The two thermistors 12 and 13, which respectively correspond to the thermistors 3 and 5, are preferably directly connected to the microprocessor. The thermistor 12 measures the skin temperature continuously and is thermally isolated from the surrounding ambient temperature. The thermistor 13 continuously measures the ambient surrounding temperature and is thermally isolated from the skin. The microprocessor 10 continuously reads the values of the thermistors and calculates oral or rectal body temperature, taking into consideration the skin temperature and the temperature of the ambient surroundings. There is typically a delay between the change of the ambient temperature and the sensing of this change by the thermistor 12 due to the isolation of the thermistor 12 from the ambient temperature and the thermal mass of the device. The length of this delay has been measured and can be up to 30 minutes. In order to improve measurement accuracy, the microprocessor stores the ambient temperature changes measured by thermistor 13 and takes into consideration the changes of ambient temperature, or in other words, the history of the ambient temperature measurements, while calculating the body temperature. An EEPROM 17 contains look-up tables taken out of experimental data of body temperature versus skin temperature, ambient temperature and changes of ambient temperature over time. The microprocessor 10 uses the look-up tables in calculating body temperature based upon the measured parameters. A method for calculating body temperature is illustrated in FIG. 5. The calculated body temperature is transmitted through a transmitter 14 (FIG. 2) and a printed antenna 15, to a remote circuit. The unit is powered by a battery 16, which is preferably a lithium battery that has a stable voltage and a long life. The battery power supply is connected to the circuit through connector 18.

Figure 3:
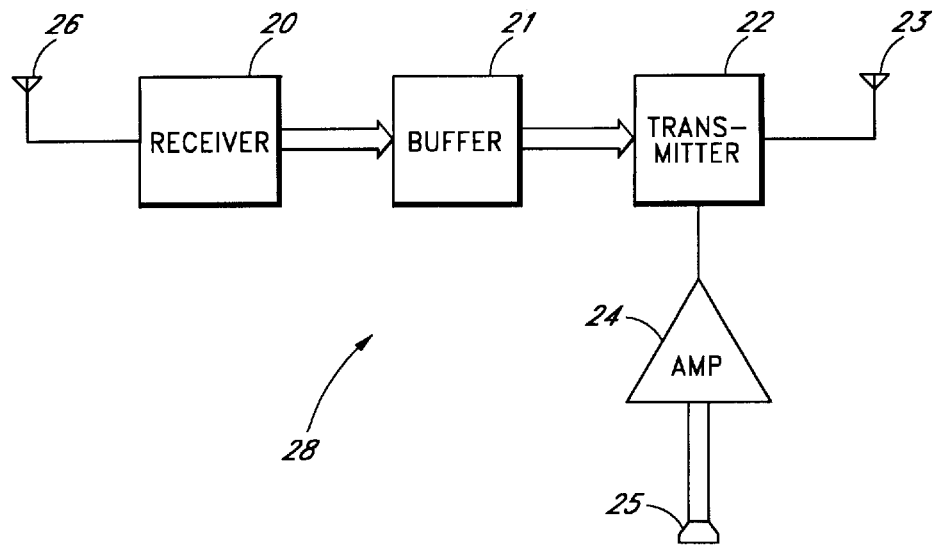
FIG. 3 is a schematic electronic drawing of the intermediate unit of the preferred embodiment.

FIG. 3 is a schematic electronic diagram of an intermediate transmitter/receiver unit 28 incorporated in the apparatus according to the preferred embodiment. The intermediate unit 28 is preferably placed close to the subject whose temperature is to be measured. The intermediate unit is used in order to save power of the measurement unit, which transmits the data to the intermediate unit. The data transmitted from the skin temperature measurement unit (shown in FIG. 2) is received through an antenna 26 and a receiver 20. The receiver 20 is connected through a buffer 21 to a transmitter 22 and an antenna 23 that transmit the data to a display and a monitoring unit (shown in FIG. 4). The intermediate unit 28 may also include a microphone 25 and an amplifier 24 to collect and transmit vocal data, in which case the system can also operate as a "Baby Monitor." All the electronic components such as the receiver 20, the buffer 21, the transmitter 22, the amplifier 24 and the microphone 25 are standard electronic components used for baby monitoring devices and are known to persons skilled in the art.

Figure 4:
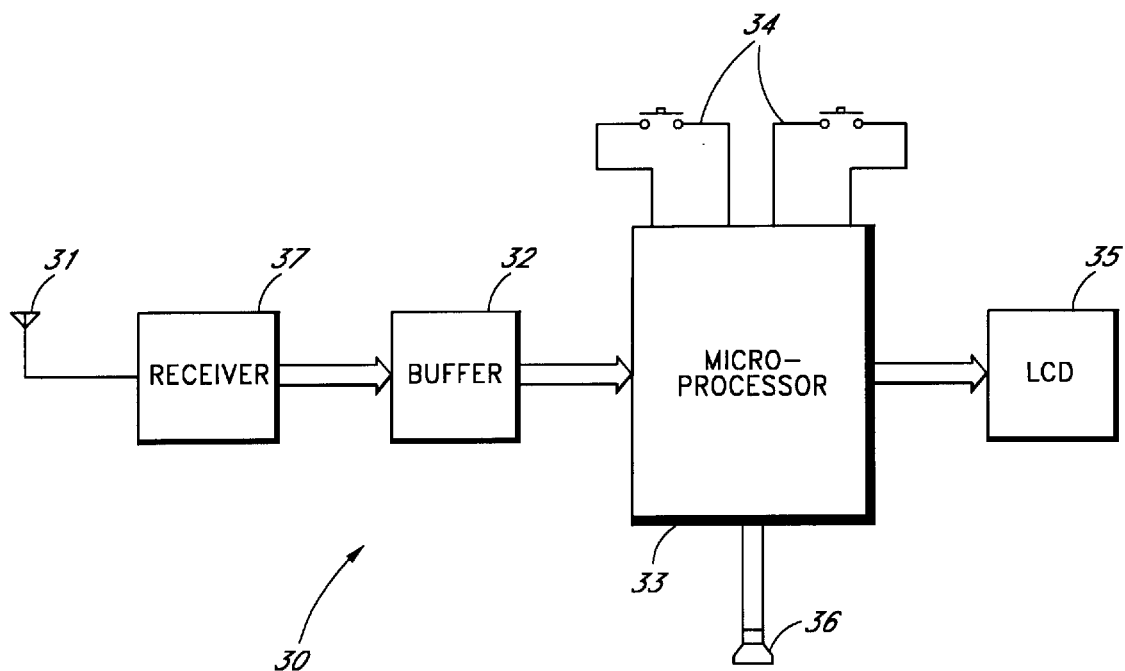
FIG. 4 is a schematic electronic drawing of the remote display and monitoring unit of the preferred embodiment.

FIG. 4 shows the electronic schematic diagram of the display and monitoring unit 30. The unit 30 receives body temperature data and vocal data from the intermediate unit (shown in FIG. 3) through an antenna 31 and a receiver 37. The receiver 37 is connected to a microprocessor 33 through a buffer 32. The microprocessor 33 processes the data and displays the temperature on the liquid crystal display (LCD) 35 and also activates the speaker 36 in case of vocal data. Two momentary push-buttons 34 are connected to the microprocessor 33 to adjust the required temperature level for an alarm. When the temperature measurement is above the alarm level, an alarm will sound through the speaker 36. The LCD 35 preferably continuously displays the subject's temperature and the alarm threshold level.

In one alternative embodiment, the microprocessor or processing unit 10 that calculates temperature can be incorporated into either the intermediate transmitter/receiver unit 28 or the monitoring unit 30. The transmitter 14 in this case can transmit raw data obtained from the sensors 12 and 13.

In one alternative embodiment, the transmitter 14 can be configured to transmit data directly to the monitoring unit 30. In this case, the intermediate unit 28 is not necessary.

Although the invention has been described in terms of certain preferred embodiments, other embodiments that are apparent to those of ordinary skill in the art, including embodiments which do not provide all of the features and advantages set forth herein, are also within the scope of this invention. Accordingly, the scope of the invention is defined by the claims that follow.

What is claimed is:

1. A temperature measurement apparatus comprising:
   a first temperature sensor configured to provide a signal related to skin temperature;
   a second temperature sensor configured to provide a signal related to ambient room temperature;
   an insulating barrier disposed between the first temperature sensor and the second temperature sensor;
   a processing unit in communication with the first and second temperature sensors, the processing unit configured to calculate body temperature based at least upon signals provided by the first and second temperature sensors; and
   a flexible printed circuit board, wherein the processing unit is disposed on the printed circuit board.

2. The apparatus of claim 1, wherein the first temperature sensor and the second temperature sensor are disposed on the printed circuit board.

3. The apparatus of claim 1, wherein the printed circuit board is embedded within the insulating barrier.

4. The apparatus of claim 1, wherein the processing unit is configured to store a plurality of readings from the second temperature sensor.

5. The apparatus of claim 1, wherein the processing unit is further configured to calculate the body temperature based at least upon a reading from the first temperature sensor and upon a reading from the second temperature sensor obtained before the reading from the first temperature sensor.

6. The apparatus of claim 1, wherein the processing unit is configured to calculate body temperature by at least referencing empirical data stored in a lookup table.

7. The apparatus of claim 1, wherein the body temperature is oral temperature.

8. The apparatus of claim 1, wherein the body temperature is rectal temperature.

9. The apparatus of claim 1, wherein the first temperature sensor and the second temperature sensor are thermistors.

10. The apparatus of claim 1, further comprising:
    a transmitter configured to transmit temperature data; and
    a monitoring unit configured to receive the temperature data and to display body temperature, wherein the body temperature is related to the temperature data.

11. The apparatus of claim 10, wherein the temperature data is the body temperature.

12. The apparatus of claim 10, wherein the transmitter is configured to transmit the temperature data directly to the monitoring unit.

13. The apparatus of claim 11, further comprising an antenna printed on the flexible circuit board.

14. The apparatus of claim 11, wherein the processing unit is disposed in the monitoring unit.

15. A temperature measurement apparatus comprising:
    a first temperature sensor configured to provide a signal related to skin temperature;
    a second temperature sensor configured to provide a signal related to ambient room temperature;
    an insulating barrier disposed between the first temperature sensor and the second temperature sensor;
    a processing unit in communication with the first and second temperature sensors, the processing unit configured to calculate body temperature based at least upon signals provided by the first and second temperature sensors;
    a transmitter configured to transmit temperature data;
    a monitoring unit configured to receive the temperature data and to display body temperature, wherein the body temperature is related to the temperature data; and
    an intermediate receiving and transmitting unit configured to receive the temperature data transmitted by the transmitter and to retransmit the temperature data to the monitoring unit.

16. The apparatus of claim 15, wherein the processing unit is disposed in the intermediate receiving and transmitting unit.

17. The apparatus of claim 15, wherein the intermediate receiving and transmitting unit comprises a microphone, and wherein the intermediate receiving and transmitting unit is configured to transmit audio signals captured by the microphone to the monitoring unit.

18. The apparatus of claim 17, wherein the monitoring unit comprises a speaker, and wherein the monitoring unit is configured to reproduce, through the speaker, audio signals received from the intermediate receiving and transmitting unit.

* * * * *